United States Patent
Karl et al.

(10) Patent No.: US 6,780,389 B2
(45) Date of Patent: Aug. 24, 2004

(54) PROCESS FOR THE PRODUCTION OF MODIFIED CARBON BLACK

(75) Inventors: Alfons Karl, Gruendau (DE); Ralph McIntosh, Hanau (DE); Werner Kalbitz, Rodenbach (DE); Horst Kleinhenz, Grosskrotzenburg (DE); Gerd Tauber, Seligenstadt (DE); Stephan Luedtke, Biebergemeund (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/201,967

(22) Filed: Jul. 25, 2002

(65) Prior Publication Data

US 2004/0018140 A1 Jan. 29, 2004

(30) Foreign Application Priority Data

Jul. 25, 2002 (DE) .......................................... 101 36 043

(51) Int. Cl.⁷ ................................................. C09C 1/56
(52) U.S. Cl. .................................. 423/449.3; 423/449.2
(58) Field of Search ............................. 423/449.2, 449.3

(56) References Cited

U.S. PATENT DOCUMENTS

| 6,214,100 B1 | 4/2001 | Parazak et al. ............. 106/31.6 |
| 2001/0004871 A1 | 6/2001 | Johnson et al. .............. 136/499 |

FOREIGN PATENT DOCUMENTS

| EP | 1 061 107 | 12/2000 |
| EP | 1 072 654 | 1/2001 |
| WO | WO 96/18688 | 6/1996 |

*Primary Examiner*—Stuart Hendrickson
(74) *Attorney, Agent, or Firm*—Oblon, Spivak, McClelland, Maier & Neustadt, P.C.

(57) ABSTRACT

A process for the production of modified carbon black, in which a carbon black dispersion containing carbon black, water and wetting agent, is mixed with an acid, aqueous solution or suspension of a primary amine and then reacted with sodium nitrite solution.

17 Claims, No Drawings

PROCESS FOR THE PRODUCTION OF MODIFIED CARBON BLACK

BACKGROUND OF THE INVENTION

1. Field of the Invention

The present invention relates to a process for the production of modified carbon black.

2. Description of the Background

A process for the surface-modification of carbon-containing material with aromatic groups by electrochemical reduction of a diazonium salt is known from EP 0569503. The production of carbon black with organic groups, by linking the carbon black with organic groups by means of a diazonium group produced via the primary amine is also known (WO 96/18688).

The known processes have the disadvantage that compounds containing both hydroxy and amino groups do not react with the carbon black.

Accordingly, there remains a need for new processes of producing modified carbon black.

SUMMARY OF THE INVENTION

It is an object of the invention is to provide a process for the production of modified carbon black.

In particular, it is an object of the present invention to provide a process in which the carbon black also reacts with compounds which contain at least one hydroxy group and at least one amino group.

The invention provides a process for the production of modified carbon black, characterized in that a carbon black dispersion, containing carbon black, water, and wetting agent is mixed with an acid, aqueous solution or suspension of a primary amine (i.e., an acidifed solution or suspension), and then reacted with a sodium nitrite solution.

Accordingly, the object of the present invention, and others, may be accomplished with a process for producing modified carbon black, comprising:

mixing (i) a dispersion comprising carbon black, water, and a wetting agent and (ii) an acidified aqueous solution or suspension of a primary amine, following by reacting the mixture with a solution of sodium nitrite.

The objects of the present invention may also be accomplished with the modified carbon black produced by the process described above.

The objects of the present invention may also be accomplished with a method of producing article by incorporating the modified carbon black of the present invention into an article.

A more complete appreciation of the invention and many of the attendant advantages thereof will be readily obtained as the same becomes better understood by reference to the following detailed description.

DETAILED DESCRIPTION OF THE INVENTION

Furnace black, gas black, channel black, lampblack, thermal black, acetylene black, plasma black, inversion black, described in DE 195 21 565 (incorporated herein by reference), Si-containing carbon blacks, described in WO 98/45361 (incorporated herein by reference) or DE 19613796 (incorporated herein by reference), or metal-containing carbon blacks, described in WO 98/42778 (incorporated herein by reference), arc furnace black and carbon blacks that are by-products of chemical production processes may be used as carbon black. The carbon black may be activated by reactions carried out in advance, for example by oxidation. Pigment blacks may also be used.

Other carbon blacks may be: conductivity carbon black, carbon black for UV stabilization, carbon black as a filler in systems other than rubber, such as for example in bitumen, plastic, black as a reduction agent, in metallurgy.

The nature of the wetting agent is not particularly limited. Anionic, cationic and/or non-ionic wetting agents may be used.

Tamol may be used as an anionic wetting agent.

Akypoquat 132 (cationic fatty ester (CTFA: Lauroyl PG-Trimonium Chloride)) from Kao Chemicals GmbH, Bayowet FT 738 VP AC 2023 (quarternary fluoroalkylammoniumiodide) from Bayer AG, DP2-7949 (aqueous solution of cationic homopolymers) from Ciba Geigy Chemicals, DP7-7961 (aqueous solution of cationic polymers) from Ciba Geigy Chemicals, DP7-7962 (aqueous solution of cationic polymers) from Ciba Geigy Chemicals, DP7-7963 (aqueous solution of cationic polymers) from Ciba Geigy Chemicals, Epikuron 200 (phosphatidyl cholin) from Lukas Meyer, (Ethoxamine SF 11 (ethoxylated fatty amine with 11 mol ethylene dioxide) from Witco, Ethoxamine SF 15 (ethoxylated fatty amine with 15 mol ethylene oxide) from Witco, Forbest 13 (neutr. compound, acid polyester and fatty alcohol) from Lukas Meyer, Forbest 610 (carboxylic acid diamine preparation) from Lukas Meyer, Magnafloc 1797 (aqueous solution of cationic crosslinked condensation resins) from Ciba Speciality Chemicals, Protectol KLC 50 (dimethyl-C 12/14-alkylbenzylammoniumchloride in water (ca 50%)) from BASF, Rewoquat CPEM (cocopentaethoxymethylammoniummethosulfate) from Witco Surfactants GmbH, Rewoquat RTM 50 (ricinoleic acid propylamido trimethylammonium methosulfate) from Witco Surfactants GmbH, Sochamine 35 (alkylimidazoline) from Witco Surfactants GmbH, may be used as a cationic wetting agent.

A compound from the group crosslinked polyoxyethyleneacrylic acid, fatty alcohol oxethylate, nonylphenolpolyglycolether, polyvinylpyrolidone, glycerol fatty acid ester, propylene glycol fatty acid ester, sorbitan fatty acid ester, Polyoxyethylenesorbitan fatty acid ester, tetraoleic acid polyoxyethylenesorbitol, polyoxyethylenealkylether, polyoxyethylenealkylphenylether, polyoxyethylenepolyoxypropylene glycol, Polyoxyethylene-polyoxypropylenealkylether, Polyethyleneglycol fatty acid ester, higher fatty alcohol esters, Polyhydric alcohol fatty acid ester, may be used as a non-ionic wetting agent.

The carbon black dispersion may be produced by dispersing the carbon black together with the wetting agent or agents in water and optionally using pearl mills, ultra-sound apparatus or an Ultra-Turrax for dispersion. After dispersion, the carbon black dispersion may be centrifuged or filtered.

As the primary amine of the formula R—$NH_2$, all amines may be used, that can form diazonium salts. The R group may be an aliphatic group and/or a cyclic, organic group. The R group may be substituted or unsubstituted, branched or unbranched. Aliphatic groups may be alkanes, alkenes, alcohols, ethers, aldehydes, ketones, carboxylic acids or carbohydrates. Cyclic, organic groups may be alicyclic hydrocarbons, for example cycloalkyls or cycloalkenyls, heterocyclic hydrocarbons, for example pyrrolidinyl, pyrrolinyl, piperidinyl, or morpholinyl, aryles, for example phenyl, naphthyl or anthracenyl or heteroaryls, for example imidazolyl, pyrazolyl, pyridinyl, thienyl, thiazolyl, furyl or indolyl. The R group may be substituted with R', OR',COR', COOR', OCOR', carboxylate, salts, for example COOLi, COONa, COOK or COO$^-$NR$^1$$_4$$^+$, OH, halogen, CN, NR'$_2$, SO$_3$H, sulfonate salts, for example SO$_3$Li, SO$_3$Na, SO$_3$K, SO$_3$$^-$NR'$_4$$^+$, OSO$_3$H or OSO$_3$$^-$salts, NR'(COR'), CONR'$_2$, NO$_2$, PO$_3$H$_2$, phosphonate salts, for example PO$_3$HNa und PO$_3$Na$_2$, phosphate salts, for example OPO$_3$HNa and OPO$_3$Na$_2$, N=NR', NR'$_3$$^+$X$^-$, PR'$_3$$^+$X$^-$, S$_k$R', SSO$_3$H, SSO$_3$$^-$salts, SO$_2$NR'R'', SO$_2$SR', SNR'R'', SNQ, SO$_2$NQ, CO$_2$NQ, S-(1,4-piperazinediyl)-SR', 2-(1,3-dithianyl) 2-(1, 3-dithiolanyl), SOR' and SO$_2$R'. R' and R" may be the same or different and H, unbranched or branched C$_1$–C$_{20}$ substituted or unsubstituted, saturated or unsaturated hydrocarbons, for example alkyl, alkenyl, alkynyl, substituted or unsubstituted aryles, substituted or unsubstituted heteroaryles, substituted or unsubstituted alkylaryles or substituted or unsubstituted arylalkyles and k may be a whole number from 1–8, preferably 2–4. The anion X$^-$ may be a halogenide or anion of a mineral or organic acid. Q may be (CH$_2$)$_w$, (CH$_2$)$_x$O(CH$_2$)$_z$, (CH$_2$)$_x$NR(CH$_2$)$_z$, or (CH$_2$)$_x$S (CH$_2$)$_z$, where w is a number from 2 to 6 and x and z are a number from 1 to 6.

In one embodiment, the R group may be an aromatic group of the formula A$_y$Ar, where Ar is an aromatic radical, for example aryl or heteroaryl, preferably phenyl, naphthyl, anthracenyl, phenanthrenyl, biphenyl, pyridinyl, benzothiadiazolyl or benzothiazolyl, A may be a substituted aromatic radical, as described above or a linear, branched or cyclic hydrocarbon radical, unsubstituted or substituted with one or more functional groups and y is a whole number from 1 up to the whole number of —CH radicals in the aromatic radical.

In a further embodiment, the R group may be substituted with ionic or ionizable groups. The ionic group may be an anionic or cationic group and the ionisable group an anion or a cation, for example sulfonic acid, phosphoric acid, carboxylic acid, sulfophenyl, preferably hydroxysulfophenyl, substituted or unsubstituted polysulfophenyl, substituted or unsubstituted sulfonaphthyl, substituted or unsubstituted polysulfonaphthyl or salts thereof, p-sulfophenyl (p-sulfanilic acid), 4-hydroxy-3-sulfophenyl (2-hydroxy-5-amino-benzenesulfonic acid), and 2-sulfoethyl (2-aminoethanesulfonic acid), a quarternary ammonium group (—NR$_3$$^+$) and quarternary phosphonium groups (—PR$_3$$^+$), quarternary cyclic amines, N-substituted Pyridine compounds, for example N-methylpyridyl, (C$_5$H$_4$N)C$_2$H$_5$$^+$,C$_6$H$_4$(NC$_5$H$_5$)$^+$,C$_6$H$_4$COCH$_2$N (CH$_3$) $_3$$^{+,C}$$_6$H$_4$COCH$_2$(NC$_5$H$_5$)$^+$,(C$_5$H$_4$N)CH$_3$$^+$ and C$_6$H$_4$CH$_2$N(CH$_3$)$_3$$^+$.

The R group may be aromatic sulfides, for example Ar(CH$_2$)$_q$S$_k$(CH$_2$) $_r$Ar' or A—CH$_2$)$_q$S$_k$(CH$_2$)$_r$Ar", where Ar and Ar' independently of each other are substituted or unsubstituted aryl or heteroaryl groups, Ar" is an aryl or heteroaryl group, k is 1 to 8 and q and r are 0–4. Substituted aryl groups may contain subsituted alkylaryl groups, preferably bis-para-(C$_6$H$_4$)—S$_2$—(C$_6$H$_4$)— or para(C$_6$H$_4$)—S$_2$—(C$_6$H$_5$) or aminophenyls, for example (C$_6$H$_4$)—NH$_2$, (C$_6$H$_4$)—CH$_2$—(C$_6$H$_4$)—NH$_2$ or (C$_6$H$_4$)—SO$_2$—(C$_6$H$_4$)—NH$_2$.

In a preferred embodiment, compounds having at least one hydroxy and at least one amino group, for example aminophenylethanol, or aminobenzenesulfonic acid, may be used as the primary amine.

To set the acid pH value of the aqueous solution or suspension of the primary amine, inorganic acids, preferably hydrochloric acid, may be used. The pH value may be lower than 6, preferably lower than 3.

The carbon black dispersion and the acid, aqueous solution of the primary amine may be mixed by stirring.

The sodium nitrite may be dissolved in water. The sodium nitrite solution may be dropped into the carbon black dispersion/amine mixture. The reaction with sodium nitrite solution may be carried out at temperatures of −5° C. to 30° C.

The carbon black dispersion produced with the process according to the invention may be used directly, depending on the application, as will be readily appreciated by those skilled in the art. The modified carbon black may be recovered from the carbon black dispersion prior to further manipulation, in one embodiment of the invention.

The modified carbon black may be used both as a filler, reinforcing filler, UV-stabilizer, conductivity carbon black and as a pigment in a variety of articles. Examples of such articles include rubber, plastic, printing colors, inks, inkjet inks, lacquers, paints, bitumen, concrete, other building materials and paper. Methods of Incorporating the inventive carbon black into these types of articles is well-known to those skilled in the art.

The process according to the invention has the advantage that it is possible to react carbon black also with compounds that contain at least one hydroxy and at least one amino group.

EXAMPLES

Having generally described this invention, a further understanding may be obtained by reference to certain specific examples which are provided herein for purposes of illustration only and are not intended to be limiting unless otherwise specified.

Reference Example 1 (according to WO 96/18688)

100 g carbon black FW 18 are suspended in 1.4 l fully desalinated water in a 33 beaker.

23.66 g 2-(4-aminophenyl)ethanol are suspended in 600 ml fully desalinated water, 18 g hydrochloric acid (37%) are diluted with 10 ml fully desalinated water and added to the amine suspension in portions. The solution becomes clear and yellowish.

10.4 g sodium nitrite, dissolved in 104 ml fully desalinated water are dropped into this solution at room temperature. This reinforces the yellow coloring, until a yellow substrate is deposited. This may be dissolved again by adding dilute hydrochloric acid. The formation of a reddish, sticky substance is then observed.

This solution is dropped into the carbon black suspension. Gas formation may be observed. A reddish sticky substance separates out on the surface.

Reference Example 2

100 g carbon black FW 18 are suspended in 1.4 l fully desalinated water in a 33 beaker.

23.66 g 2-(4-aminophenyl)ethanol are suspended in 600 ml fully desalinated water, 18 g hydrochloric acid (37%) are diluted with 10 ml fully desalinated water and added to the amine suspension in portions. A yellowish, clear solution forms, which is added to the carbon black suspension whilst stirring.

10.4 g sodium nitrite are dissolved in 104 ml fully desalinated water and dropped into the mixture of carbon black suspension and aminophenylalcohol in ca 3 hours. During this process, the formation of bubbles may be observed. After stirring overnight (ca 20 hours), the suspension is transferred to two evaporating dishes and evaporated in a waste air drying cabinet for ca 16 hours at 70° C. until completely dry.

The modified carbon black is ground in two portions for a minute each in a laboratory mixer at level III (maximum).

The carbon black cannot be dispersed and stabilized even using wetting agents such as Hydropalat 3065 or Tamol. The individual carbon black particles are glued firmly together with "polymers" that have formed, in such a way that this carbon black, in contrast to normal carbon black, cannot be dispersed by ultrasound.

Reference Example 3

100 g carbon black FW 18 are suspended in 1.4 l fully desalinated water in a 33 beaker.

12 g 2-(4-aminophenyl)ethanol are suspended in 400 ml fully desalinated water. 9 g hydrochloric acid (37%) are diluted with 20 ml fully desalinated water and added to the amine suspension in portions. A clear, yellowish solution forms, which is added to the carbon black suspension whilst stirring.

7.2 g sodium nitrite are diluted in 100 ml fully desalinated water and dropped into the carbon black suspension and the aminophenyl alcohol in ca 2 hours. During this process, the formation of bubbles can be observed. After stirring overnight (ca 20 hours), the suspension is transferred to two evaporating dishes and evaporated in a waste air drying cabinet for ca 16 hours at 70° C. until completely dry.

The modified carbon black is ground in two portions for one minute each in a laboratory mixer at level III (maximum).

In spite of the significantly lower concentrations of aminophenyl alcohol, there are no improvements in relation to reference example 2. The carbon black is not self-dispersing and cannot be dispersed even with wetting agents.

Example 1

100 g carbon black FW 18 is mixed into and predispersed in the solution of 26.7 g Tamol in 540 g water with the Ultra Turrax running (10 000 RPM) (30 min). This is then dispersed twice with ultrsound in continuous flow. No particles >1$\mu$ can be detected under the light microscope.

12 g 2-(4-aminophenyl)ethanol are suspended in 400 ml fully desalinated water. 9 g hydrochloric acid (37%) are diluted with 20 ml fully desalinated water and added to the amine suspension in portions. A clear, yellowish solution forms, which is added to the carbon black dispersion whilst stirring.

7.24 g sodium nitrite are dissolved in 100 ml fully desalinated water and dropped into the mixture of carbon black dispersion and aminophenyl alcohol in ca 1 hour. This is stirred overnight.

Example 2

100 g carbon black FW 18 is mixed into and predispersed in the mixture of 66.6 g Hydropalat 3065 in 500 g water with the Ultra Turrax running (10,000 RPM) (30 min). This is then dispersed twice with ultrasound in continuous flow. No particles >1$\mu$ can be detected under the light microscope.

12 g 2-(4-aminophenyl)ethanol are suspended in 400 ml fully desalinated water, 9 g hydrochloric acid (37%) are diluted with 20 ml fully desalinated water and added to the amine suspension in portions. A clear, yellowish solution forms, which is added to the carbon black dispersion whilst stirring.

7.24 g sodium nitrite are dissolved in 100 ml fully desalinated water and dropped into the mixture of carbon black dispersion and aminophenyl alcohol in ca 2 hours. There is a strong foam formation. The mixture is stirred overnight.

A refrigeration-stable carbon black dispersion is obtained.

Example 3

100 g carbon black FW 18 are mixed into and predispersed in the mixture of 66.6 g Tego Dispers 750W in 500 g water with the Ultra Turrax running (10,000 RPM) (30 min). This is then dispersed twice with ultrasound in continuous flow. There is a strong foam formation. No particles >1$\mu$ can be detected under the light microscope.

20 g Sulfanilic acid are dissolved in 700 ml fully desalinated water at 65° C. After cooling, the solution remains clear, although it is supersaturated. This solution is added to the carbon black dispersion whilst stirring.

8.8 g sodium nitrite are diluted in 100 ml fully desalinated water and dropped into the mixture of carbon black dispersion and sulfanilic acid in ca 2 hours. There is a strong formation of foam, which is defoamed by the addition of 1 ml UCO Foamaster 110.DE. The mixture is stirred for 4 days.

A refrigeration-stable and storage-stable carbon black dispersion is obtained after the addition of AMP 9.

The carbon black FW 18 is a commercial product of Degussa.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No 101 36 043.6, filed on Jul. 25, 2001, and incorporated herein by reference in its entirety.

What is claimed is:

1. A process for producing modified carbon black, comprising:
    mixing (i) a dispersion comprising carbon black, water, and a wetting agent and (ii) an acidified aqueous solution or suspension of a primary amine, following by
    reacting the mixture with a solution of sodium nitrite.

2. The process of claim 1, wherein the carbon black is gas black.

3. The process of claim 1, wherein the primary amine also contains at least one hydroxy group.

4. The process of claim 1, wherein the wetting agent is anionic.

5. The process of claim 1, wherein the wetting agent is cationic.

6. The process of claim 1, wherein the wetting agent is non-ionic.

7. The process of claim 1, wherein the carbon black is selected from the group consisting of furnace black, channel black, lampblack, thermal black, acetylene black, plasma black, inversion black, Si-containing carbon blacks, metal-containing carbon blacks, arc furnace black, and carbon blacks that are by-products of chemical production processes.

8. The process of claim 1, wherein the primary amine is represented by the formula $R-NH_2$, wherein the R group is an aliphatic group and/or a cyclic, organic group.

9. The process of claim 1, wherein the primary amine is aminophenylethanol or aminobenzenesulfonic acid.

10. The process of claim 1, wherein (ii) has a pH lower than 6.

11. The process of claim 1, wherein (ii) has a pH lower than 3.

12. The process of claim 1, wherein (ii) is acidified with an inorganic acid.

13. The process of claim 1, wherein (ii) is acidified with hydrochloric acid.

14. The process of claim 1, wherein the reaction with the sodium nitrite is conducted at a temperature of −5 to 30° C.

15. The process of claim 1, further comprising recovering the modified carbon black.

16. A method of producing an article containing a modified carbon black, comprising:

producing a modified carbon black according to the process of claim 1, and then incorporating the modified carbon black into an article.

17. The method of claim 16, wherein the article is selected from the group consisting of rubber, plastic, printing colors, inks, inkjet inks, lacquers, paints, bitumen, concrete, building materials, and paper.

* * * * *